United States Patent [19]

Veltri

[11] Patent Number: 4,518,611
[45] Date of Patent: May 21, 1985

[54] 2-FURYLBUTYROLACTONE MODULATION OF THE IMMUNE SYSTEM IN MAMMALS

[75] Inventor: Robert W. Veltri, West Chester, Pa.

[73] Assignee: National Foundation for Cancer Research, Inc., Bethesda, Md.

[21] Appl. No.: 536,995

[22] Filed: Sep. 29, 1983

Related U.S. Application Data

[63] Continuation-in-part of Ser. No. 481,998, Apr. 4, 1983, abandoned, which is a continuation-in-part of Ser. No. 449,584, Dec. 14, 1982, abandoned.

[51] Int. Cl.³ .................... A61K 31/34; A61K 31/335
[52] U.S. Cl. .................................. 514/470; 514/472; 549/473; 514/473

[58] Field of Search ................. 424/285, 279; 549/473

[56] References Cited

U.S. PATENT DOCUMENTS 4,238,500 12/1980 Szent-Györgi et al. ............ 424/278
4,287,205 9/1981 Szent-Györgi et al. ............ 424/278

Primary Examiner—Leonard Schenkman
Attorney, Agent, or Firm—Omri M. Behr

[57] ABSTRACT

Compositions containing compounds which exhibit immunomodulatory properties can be used as immunostimulants or immunosuppressants in humans and animals.

16 Claims, 1 Drawing Figure

FIG. 1.

2-FURYLBUTYROLACTONE MODULATION OF THE IMMUNE SYSTEM IN MAMMALS

This application is a continuation-in-part application of copending application Ser. No. 481,998, filed Apr. 4, 1983, which is in turn a continuation-in-part application of copending application Ser. No. 449,584, filed Dec. 14, 1982 both abandoned.

RELATED CASES

This application is related to application Ser. No. 536,993 abandoned of Szent-Györgyi and Fodor, filed concurrently herewith which is in turn a continuation-in-part of pending application Ser. No. 450,493, filed Dec. 16, 1982, which is in turn a continuation of application Ser. No. 192,806, filed Oct. 1, 1980, now abandoned, which is in turn a divisional of application Ser. No. 093,594, filed Nov. 13, 1979, now U.S. Pat. No. 4,287,205, which is in turn a continuation of application Ser. No. 917,327, filed June 20, 1978, now abandoned. This application is also related to pending application Ser. No. 192,815, of Szent-Györgyi and Fodor, filed Oct. 1, 1980, which is in turn a divisional of application Ser. No. 093,594, filed Nov. 3, 1979, now U.S. Pat. No. 4,287,205, which is in turn a continuation of application Ser. No. 917,327, filed June 20, 1978, now abandoned and to application Ser. No. 536,994, of Fodor, filed concurrently herewith, which is in turn a continuation-in-part of application Ser. No. 478,331, filed Mar. 24, 1983.

BACKGROUND OF THE INVENTION

The present invention relates generally to chemical compounds and compositions and their use as immunomodulatory agents.

Copending applications, Ser. No. 536,993 and Ser. No. 536,994, disclose the formation of novel compounds, one use for which is also disclosed herein. These compounds are produced by reacting approximately equal amounts of compound of the general formula wherein $R_1$ and $R_2$ are selected from the group consisting of hydrogen and lower alkyl, provided that at least one is hydrogen; wherein $R_3$ and $R_4$ may be the same or different and are selected from the group consisting of lower alkyl and aryl; wherein $R_5$ and $R_6$ are selected from the group consisting of hydrogen and lower alkyl and may be the same or different and a compound of the general formula wherein X is selected from the group consisting of O, S, and NH; wherein $R_7$ and $R_8$ are selected from the group consisting of hydrogen and lower alkyl and may be the same or different. wherein $R_7$ may be wherein $R_9$ is selected from the group consisting of wherein $R_{10}$ and $R_{11}$ are selected from the group consisting of hydrogen, lower alkyl, phenyl and hydroxy substituted lower alkyl and may be the same or different obtaining the product of the reaction, treating the product with acid anhydride or acid amide, refluxing and crystallizing the novel compounds. Recovery of the pure product may be facilitated by treatment or purification of the intermediate by any of the several techniques known to one of ordinary skill in the art such as, for example, charcoal filtration, ion exchange or gel chromotography.

The novel compounds produced by the above described process include wherein $R_2$ is selected from the group consisting of hydrogen and lower alkyl; wherein $R_5$ and $R_6$ are selected from the group consisting of hydrogen and lower alkyl and may be the same or different; wherein $R_7$ and $R_8$ are selected from the group consisting of hydrogen and lower alkyl and may be the same or different; wherein $R_7$ may be wherein $R_9$ is selected from the group consisting of wherein $R_{10}$ and $R_{11}$ are selected from the group consisting of hydrogen, lower alkyl, phenyl and hydroxy substituted lower alkyl and may be the same or differ- ent; wherein when $R_7$ contains a hydroxyl group in the α, β, or γ position, $R_7$ may form the hemiketal ring closure at carbon 3 of the butyrolactone with protonation of the carbonyl group on the same carbon atom; wherein n is selected from the group consisting of 1, 2, and 3; and wherein X is selected from the group consisting of O, S, and NH.

Lactone ring formation, wherein $R_2$, $R_5$, $R_6$, $R_{10}$, X and n are as described above can occur. These rings will ordinarily partially rearrange, in aqueous or highly polar media to give tautomeric equilibrium products wherein $R_2$, $R_5$, $R_6$, $R_7$, $R_8$, $R_{10}$, $R_{11}$, X and n are as described above.

The compounds disclosed in Ser. No. 1 and Ser. No. 2 can be formulated with generally known pharmaceutical carriers into compositions which can be administered to animals and humans. These compositions show immunomodulatory and cytotoxic activity at very low accute toxicity values.

It is believed that the cytotoxic activity of these compositions may be attributable to stimulation of the immune system by the compounds or to the cytoxicity of the compounds per se or to a combination of both effects.

Because of their cytotoxic activity, these compositions may be used in cancer therapy for a broad range of cancers. The compositions may be used in immune therapy of depressed immune systems, as in the case of AIDS (Acquired Immune Disorder Syndrome).

The immune system is one of the primary defenses against disease bearing microbes and other foreign protein in higher animals. An immune response is mediated by the action of specific antibody proteins which react to specific antigens. Antigens are substances of fairly high molecular weight, often proteins, which are foreign to an individual's body. They are most frequently located on the outer surfaces of cells. Potential antigens can be found on pollen grains, tissue grafts, synthetics, animal parasites, viruses, and bacteria.

In humans, many potential antigens never pass the body's first two defense lines and therefore never trigger the immune system. These two defense lines consist firstly of the skin, mucous membranes, tears, and stomach acid and secondly of specialized white blood cells, granulocytes and monocytes, and macrophages which destroy pathogens and other potential antigens by phagocytosis, that is by engulfing and destroying the foreign material. These white blood cells and macrophages are called phagocytes. When pathogens or other foreign substances do pass the body's first two defense lines, the immune response begins.

There are two principal immune defense systems, humoral and cellular, both of which react to antigens. Humoral immunity is due to circulating antibodies which are found in the gamma globulin fraction of the plasma proteins. When plasma is centrifuged at high speeds its component proteins separate by weight into sections called fractions. Antibodies are usually found in the fraction whose components have a molecular weight of approximately 156,000. This particular fraction has been named the gamma globulin fraction. Humoral immunity forms a major defense against bacterial infections. Cellular immunity is partly due to lymphocyte products called lymphokines. This type of immunity is responsible for delayed allergic reactions, rejection of transplants of foreign tissue, and rejection of tumor cells. It is the major defense against infections due to viruses, fungi, and a few bacteria such as the tubercle bacillus.

Specialized white blood cells called lymphocytes are responsible for both humoral and cellular immunity. Lymphocyte precursor cells are made in the bone marrow of adult humans followed by migration to various organs or in the yolk sac of a developing fetus followed by migration into the fetus and then to various organs. In humans, some of these precursor cells migrate to the thymus, which is a two-lobed, glandular appearing structure located in the upper chest just behind the sternum, where they are transformed into T-lymphocytes which are involved in cellular immunity. In humans, the rest of the precursor cells migrate to the spleen where they are transformed into B-lymphocytes which are involved in humoral immunity. The T- and B-lymphocytes are structurally indistinguishable although they function differently and can be distinguished through various chemical means. The mature lymphocytes circulate in the blood and can also be found in the lymph nodes as well as the spleen and thymus.

Humoral immunity is mediated by the B-lymphocytes which have receptors for particular antigens on their cell surfaces. They seem to be very specific and each type of B-lymphocyte reacts to only one antigen. When bacteria or viruses, for example, invade an organism, B-lymphocytes react to and combine with the antigens on the bacterial or viral surface and the lymphocyte is stimulated to divide. Its daughter cells are transformed into specialized cells called plasma cells. These cells produce and then secrete large quantities of antibodies into the general circulation. The antibodies are specific for the antigens which stimulated their production and react only with those antigens. Antibodies known as agglutinins cause several antigen containing substances to agglutinate or clump together. This keeps the substance from spreading to the tissues and allows the phagocytes to capture or the lymph nodes to filter the invading material. Other antibodies act by opening holes in bacterial cell walls, thereby killing the bacteria.

These are known as lysins. Antibodies called antitoxins combine with toxins produced by bacteria and thereby neutralize them.

Once a pathogen invades the body and the immune response begins, antibodies can be made in several hours. This initial reaction is called the primary response or primary immunization. However, during that time, the pathogens have also been dividing and sometimes producing toxin, either of which results in various disease symptons. It may take days or weeks before enough antibodies are made to eliminate all the pathogens but one they disappear, the disease symptoms disappear as well. The lymphocytes, plasma cells, and antibodies remain and circulate in the blood so that if the same pathogens enter the body a second time, the lymphocytes react immediately and start antibody production. The response of the sensitized lymphocytes is called the secondary response. The secondary response results in the production of higher levels of antibody than were produced during the primary response. So many antibodies are produced so rapidly that the microbes are unable to divide and cause disease. Humoral immunity is known as immediate hypersensitivity due to the fact that a previously exposed organism can respond within minutes to an antigen, as in the case of hay fever. Another example of immediate hypersensitivity would be anaphylactic shock, an extreme allergic reaction that sometimes occurs when an individual is exposed to an antigen to which he has been sensitized. At times, this humoral response to the antigen can result in death.

Humoral immunity can be both naturally and artificially induced. In the case of active natural immunity, an individual's lymphocytes continue to circulate and activate the production of antibodies after an infection. This active natural immunity lasts for many years or even a lifetime. An infant receives antibodies from the colostrum, milk secreted by the mother, the first few days after birth, which gives it immunity the first year of its life. This is known as passive natural immunity since the infanct is not involved in the actual production of the antibodies. Active artificial immunity is induced by injecting dead or weakened microbes into an individual. Their surface antigens can still trigger lymphocyte production of antibodies but these microbes do not cause the disease symptoms that their more virulent forms do. When the individual is later exposed to the virulent microbe, he is already sensitized and immediately responds with a massive production of antibodies. Active artificial immunity may last many years or permanently with booster shots. There is also a form of passive artificial immunity which provides protection for about one month. This temporary immunity is brought about by injecting antibodies obtained from another person or animal into an individual. It is usually only used in crisis situations and epidemics. Because the lymphocytes are bypassed, they neither make antibodies nor "remember" the antigen, which accounts for the temporary effect of this method.

In cellular immunity, as contrasted to humoral immunity, circulating antibodies are not detectable. The T-lymphocytes which mediate this type of immunity are activated when they encounter antigens on cells from another individual, as in the case of transplants, tumors, or viruses. Like B-lymphocytes, T-lymphocytes are specific and each type reacts with only one antigen. The lymphocytes enlarge, divide, and produce lymphokines which participate in the attack on the foreign protein. They also stimulate the phagocytic activity of macrophages. Although immunological memory exists as with humoral immunity, the response is much slower. It may take as long as ten or twelve hours to develop a response in a previously sensitized individual and cellular immunity is therefore known as delayed hypersensitivity. The allergic reaction to poison ivy, oak, and sumac, the red splotch seen in a positive tuberculin skin test, and rejection of transplant tissue are all cellular immune responses.

Immunomodulating agents activate or inhibit the process of lymphocyte proliferation. Normal lymphocyte proliferation is due to various interactions between antigens, macrophages, T- and B-lymphocytes as well as certain chemicals. For example, the presence of a particular antigen activates a particular T- or B-lymphocyte. Additionally, certain B-lymphocytes can be activated by active T-lymphocytes while others are independent of the T-lymphocytes and are activated only by antigens. Activated T-lymphocytes can cause macrophages to produce a molecule known as interleukin 1(IL-1) which inturn activates both T- and B-lymphocytes. Activated T-lymphocytes can also produce a molecule known as interleukin 2(IL-2) which further induces T-lymphocyte activation. Chemicals, called mitogens can trigger DNA synthesis and mitosis, which are signs of activity in T- or B-lymphocytes. Some mitogens affect only one type of lymphocyte while others affect many types. Immunomodulating agents of various kinds and in varying amounts affect the complex interactions between the components of the immune system. As will be shown, the compounds and compositions of this invention act as immune stimulators or suppressors, depending upon the dosage, and affect both T- and B-lymphocytes.

Although the immune system is a major defense against substances which can cause disease, it cannot distinguish between helpful and harmful foreign substances and destroys both. It would be useful in many instances to have a means of regulating the immune system without harming the individual. The compounds and compositions of this invention exhibit such modulating or regulatory effects and have potential for use in the treatment of various immune disorders.

The immune system has been linked to some aspects of aging and may be important in protecting against cancer. The system is necessary for the recognition of changing or aging cells, such as worn out red blood cells, and their subsequent destruction, and for this reason is vital to normal body functions. One theory in the case of cancer is that the transformation of cells to the malignant state may occur fairly frequently but these changed cells are recognized as "not self" and destroyed. Some carcinogens may work by depressing the immune response rather than by transforming cells themselves to a malignant state. This would mean that the body would no longer destroy the naturally transformed cells and a cancerous growth could result. Immunostimulation could be useful in treating cancers of this type. When used as adjunctive therapeutic agents in chemo- or chemoimmuno-therapy, the compounds and compositions of this invention can affect the growth of tumors.

Some of the methods of treating cancer, surgery, chemotherapy, and radiation for example, can result in a suppression or drastic variation of the normal functions of the immune system. Immunostimulatory drugs, such as the compounds and compositions of this invention, can be very effective in combating and/or preventing various infections which can result due to the depressed immune system. Some immunomodulating agents which are currently being studied for use in these situations are cyclosporin-A, levamisole, and isoprinosine (inosiplex). The compounds and compositions of this invention will be novel therapeutic tools for use in this and other situations involving the immune system.

There are times when the individual's immunological response causes more damage or discomfort than the invading microbes or foreign material, as in the case of allergic reactions. Suppression of the immune response in these cases would be desirable.

Occasionally, the immunological mechanisms become sensitized to some part of the individual's own body causing interference with or even destruction of that part. The ability to distinguish between "self" and "not self" is impaired and the body begins to destroy itself. Some examples of these autoimmune diseases in man are rheumatoid arthritis, certain hemolytic anemias, rheumatic fever, thyroiditis, ulceractive colitis, myesthenia gravis, glomerulonephritis—a kidney disease, allergic encephalomyelitis, continuing nerve and liver destruction which sometimes follows viral hepatitis, and possibly multiple sclerosis. Some forms of autoimmunity come about as the result of trauma to an area usually not exposed to lymphocytes such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-react with, the individual's own tissue. Rheumatic fever is an example of this type of disease in which the antigen of the streptococcal bacterium which causes rheumatic fever is cross-reactive with parts of the human heart. The antibodies cannot differentiate between the bacterial antigens and the heart muscle antigens and cells with either of those antigens can be destroyed. Suppression of the immune system in these autoimmune diseases could be useful in minimizing or eliminating the effects of the disease.

Circulating antibodies and cellular immune responses play a role in the rejection of transplanted tissues and organs. Unless the donor is the identical twin of the recipient or is the individual himself, the recipient's lymphocytes recognize the transplant as "not self" and immediately respond to destroy it. The exceptions to this situation are transplants to non-vascularized areas (privileged sites), such as the cornea of the eye, where lymphocytes do not circulate and therefore are not sensitized and do not prompt an immune response. It is currently difficult to suppress the immune reaction to prevent rejection of the transplant without severly damaging the patient in other ways. The patient must also be given massive doses of antibiotics because his own defenses against infection have been suppressed. The compounds and compositions of this invention could be valuable in establishing tolerance to the transplant through controlled modulation of the immune system.

Because of the immune system's vital roles in defense against disease and in normal body functions, compounds and compositions, such as those disclosed in this invention, which can enhance or diminish that role are of importance. They are particularly useful when the normal action of the system has been disturbed or has caused the destruction of harmless foreign materials. They can also assist by stimulating the system's response to harmful antigens and, thus, shorten the course of various diseases.

OBJECTS OF THE INVENTION

An object of the present invention is to provide compounds having immunomodulatory activity.

Another object of this invention is to provide novel compositions effective in the treatment of immune disorders and methods for the application of such compositions.

Other objects, advantages and novel features of the present invention will become apparent from the following detailed description.

The description of the novel invention described herein includes reference to the following figures.

DESCRIPTION OF THE INVENTION

The compositions, when administered to mammalian lymphocytes, have a profound effect on their ability to reproduce as measured by their ability to synthesize DNA. This effect is bimodal. In higher concentrations, the compositions act as immunosuppressants while in lower concentrations they act as immunostimulants.

This immunomodulatory effect is seen in vitro in human blood lymphocytes and in vivo and in vitro in mouse spleen lymphocytes.

Various immunomodulatory studies have been conducted using these compositions. In these studies, T- and B-lymphocytes are isolated from human blood and mice spleens. Five strains of mice are used as lymphocyte donors, BALB/C, C57BL/6, BDF$_1$, SJL/J and DBA/2. The lymphocytes are then treated with plant proteins called lectins which act as mitogens.

Mitogens are substances which stimulate DNA synthesis and mitosis. The mitogens used in these studies were phytohemagglutinin (PHA) which is isolated from the red kidney bean and concanavalin-A (Con-A) which is isolated from the jack bean. Con-A binds to specific receptors (glycoproteins) containing-mannosyl or -glycosyl moieties and stimulates all murine T-cells to synthesize DNA, divide, and release lymphokines. Con-A in a soluble form allows distinction between T- and B-cells in the mouse, because although both T- and B-cells can bind $10^6$ molecules of Con-A per cell, only T-cells are stimulated when this lectin is presented in a soluble form. PHA stimulates only subpopulations (T$_2$ cells) of T- or B-cells. In the mouse, PHA activates a subpopulation of T-cells and does not stimulate B-cells. In humans, both T- and B-cells are probably stimulated. The activation of B-cells may be indirect and mediated by the release of soluble mediators from PHA-activated T-cells.

At doses ranging from 0.001 μg to 100 μg, the compounds of this invention have profound effects on lymphocyte mitogenesis when tested directly in vitro versus human lymphocytes. At lower doses, 0.001 to 1 μg, there is stimulation, above control levels, of PHA or Con-A mediated mitogenesis. At high doses, 10 to 100 μg, there is a profound suppression of the mitogenetic activity of lymphocytes treated with mitogens PHA and Con-A.

In vivo treatment of C57BL/6 mice comprising intraperitoneal (i.p.) administration of varying doses of the compounds for 4–12 days and subsequent testing of spleen lymphocytes with PHA and Con-A reveal a similar pattern to that of the in vitro system at doses of the compounds of 400 and 800 mg/kg versus 50 to 200 mg/kg. The observed suppression, at high doses, or stimulation, at low doses, showed statistically significant differences, with $P<0.05$.

Other experiments have been done to test the effect of the compounds on the antibody response to specific antigens, bovine serum albumin and keyhole limpet hemocyanin. It is found that high doses of the compounds do not inhibit the secondary immune response to the antigen but instead significantly enhance this response. Such doses, which routinely suppressed the in vivo and in vitro cell mediated response to mitogens did not significantly suppress humoral immunity. These data demonstrate the possibility of regulation of specific antibody production through immunostimulation.

In the experiments described below, the trends observed with high doses suitably 300 to 1000 mg/kg or low doses suitably 10 to 200 mg/kg of the compound follow the general pattern noted above. However, differences can be noted in the actual response to the compounds of PHA versus Con-A stimulated lymphocytes. This may be due to the fact that Con-A and PHA do not stimulate the same kinds of lymphocytes. Differences can also be noted in the responses of the various strains of mice. These could reflect genetic variation with respect to response of lymphocytes to mitogens. Differences observed in the in vivo versus in vitro response can be due to differences in in vivo and in vitro metabolism and to the difference between the human and murine lymphocytes.

In all these experiments, it should be noted that control cultures not stimulated with mitogens or specific antigens, and which, therefore, could be considered resting cells, are not affected by the compounds. The dramatic stimulatory or inhibitory effects are only demonstrated in cells with active DNA synthesis, that is those cells undergoing cell division.

Tests were also done to determine the immunomodulatory effects of the compounds on the cytotoxic lymphocyte activity of sensitized lymphocytes obtained from tumor dormant DBA/2 mice. The experimental model involved establishment of the dormant state in DBA/2 mice and then conducting studies to assess the effect of the compounds disclosed in this invention on the tumor dormant state. The animal model described above, mimics a suspected tumor dormant state that is suggested by clinical observations of human recurrent breast tumors and melanomas many years after apparent cure of the primary tumors.

A. Lymphocyte Stimulation Assay Protocols

The purpose of this assay is to challenge lymphocytes in microcultures with one or more polyclonal mitogens at concentrations that will induce mitogenesis within 72 hours of stimulation.

In the mouse model, spleens are removed from different strains of mice and the spleen cells are teased free and suspended in RPMI-1640 tissue culture medium at a concentration of usually $1 \times 10^7$ ml. These cells are dispensed at a concentration of $5.0 \times 10^5$ cells per microculture well in a 96 well flat bottom 96 well tissue culture plate. All testing of the compounds of this invention or mitogens are done in replicates of 10. The cells are then treated with PHA, Con-A, specific antigens, or buffer only. If in vitro testing is done, varying concentrations of the compounds of this invention or buffer only are added to the cells as well. After treatment with the mitogens and/or compounds of this invention, the cells are incubated for 72 hours. The response of these cells to mitogens and/or the compounds of this invention is assessed using $^{14}$C-thymidine labeling on the fourth day at a concentration of 0.01 $\mu$Ci/well. The labeled cells are harvested using a lymphocyte harvestor and placed onto fibrous paper discs. A scintillation cocktail is added to vials containing the discs and the results are obtained using a LKB-liquid scintillation counter (Model 1216/Rackbeta II). The data is expressed as a ratio of the cpm of the mitogen stimulated group to the control (nonmitogen) treated group=lymphocyte stimulation index (LSI).

The lymphocyte stimulation assay may be performed directly on spleen cells obtained from various strains of mice not treated with the compounds of this invention or on lymphocytes obtained from human plasma. In such experiments, the compounds of this invention are added directly to the spleen lymphocytes in vitro and the assay is completed and results interpreted. Alternatively, the mice may be treated in vivo with the compounds of this invention by intraperitoneal multi-dose schedules, followed by sacrifice and harvesting spleen lymphocytes. These cells are then tested for their response to polyclonal mitogens or specific antigens used to immunize the mice. In this system however, no additional compound is added to the in vitro lymphocyte stimulation assay system.

B. The Secondary Response Studies

The effect of the compounds of this invention on the immune response to specific antigens involves immunization of mice with specific antigens such as bovine serum albumin (BSA) or keyhole limpet hemocyanin (KLH). Following immunization, it is possible to assess the cell-mediated or humoral (antibody) immune response to these antigens by various methods:

(1) Lymphocyte stimulation assays can be performed using varying concentrations of the specific antigens as mitogens in the lymphocyte stimulation microculture system described above. The only difference is that the incubation period is extended to five days instead of three as for the polyclonal mitogens.

(2) Antibody response to soluble antigens such as BSA or KLH can be quantitated using a micro-ELISA solid phase heterogeneous immunoassay. The assay can be designed to quantitate class specific immunoglobulins (i.e., IgG or IgM).

Results of the humoral (antibody) response to BSA are obtained using a solid phase heterogeneous sandwich ELISA micromethod in 96 well Immulon microtiter plates. The cut-off for the titer was the highest dilution of mouse serum yielding on $O.D. \leqq 0.1$ when read on the MR-600 Dynatech micro-ELISA reader.

C. Measurement of Cytotoxic Lymphocyte Activity—Method

A mixed lymphocyte tumor culture (MLTC) immunoassay, used to determine the cytotoxic lymphocyte (CTL) activity employs lymphocytes from either immunized (sensitized) mice or DBA/2 tumor dormant state animals in various stages of the tumor dormant state (TDS). The assay employs L5178Y target cells labeled with $^{51}$Chromium and effector cells (sensitized lymphocytes) from the above-mentioned sources. Effector-target cell ratios will vary with different experimental conditions and may or may not include irradiated stimulator L5178Y cells. Results are expressed as % lysis of target cells based on ratio of cpm of test group over cpm of total release (maximum) both of which are corrected for spontaneous release of $^{51}Cr$. The assay can be performed as an 8 or 18 hour release assay.

In order to induce the tumor dormant state (TDS), a large group of DBA/2 mice is injected subcutaneously with $1 \times 10^6$ viable L5178Y leukemia cells subcutaneously on the midventral side of the abdomen. Ten days later the resultant tumor nodule, about 1 cm in size, is surgically excised. If the excision was successful, no subcutaneous tumors develop at the site of implantation. Seven days postexcision, the mice are challenged with 50,000 viable L5178Y leukemia cells, a dose that routinely produces death due to ascitic tumors in 100% of normal DBA/2 mice within 14 days. Immune mice resisted rapid outgrowth of the challenge L5178Y dose and remained clinically normal for many weeks thereafter. These mice are considered to be in the tumor dormant state.

D. Anti-cancer Studies—Method

Mice of the $BDF_1$ strain are given in i.p. inoculation of $10^6$ L-1210 leukemia cells on day 0. Twenty-four hours later, groups of 7 mice each are started on a nine day treatment regimen of various doses of the compounds of this invention. The experiment is continued according to the guidelines provided under the National Cancer Institute protocol for screening new anti-cancer agents and T/C ratios (median or mean survival time of treated groups over median or mean survival time of controls) are calculated. A T/C value $\geq 1.25$ (or 125%) is considered significant anticancer activity.

EXAMPLE 1

93 g 2-methyl-2,5-dimethoxy-dihydrofuran (N. Clauson-Kaas and F. Lindborg (1947) *Acta Chem. Scand.* 1: 619. was added under vigorous mechanical stirring to a solution of 75 g L-ascorbic acid in 750 ml water at room temperature. The furan was used in 50% excess. The solution became homogeneous within 15–20 minutes. The reaction was monitored by a high pressure liquid chromograph equipped with a UV detector. The original peak of Rf 1.6 of L-ascorbic acid at 254 nm in 20% aqueous methanol disappeared while a new peak appeared at Rf 5.9 to 6.0, under 64 atmospheres. It was simultaneously observed that the solution did not consume any more iodine which is indicative of the total disappearance of L-ascorbic acid.

After standing overnight at 20° C. the aqueous solution was freeze-dried to give a pale yellow foam. The latter showed well defined IR, $^{13}C$ NMR and $^{1}H$ NMR spectra.

Next, 64.0 g (0.25M) of the crude product (melting point 55° C.) and 25.0 g (0.25M) of succinic anhydride were placed into a 1 liter round-bottomed flask equipped with a reflux condenser and a nitrogen inlet tube. After adding 200 ml of HPLC-grade ethyl acetate, the reaction mixture was refluxed for 4 hours. The homogenous solution was cooled to room temperature and then placed in an ice-water bath. A white precipitate formed which was filtered by suction and washed with a few ml of cold ethyl acetate to give 29.9 g of the crude product (yield 46.6%). The filtrate was concentrated to half volume and cooled in an ice-water bath. The second crop of precipitate was again filtered to give 13.5 g of solid which contained some unreacted succinic anhydride.

The product was recrystallized from a solvent mixture (ethyl acetate/chloroform: 20/80) to give a total yield of 22.5 g (yield 35.2%) of pure product (long white needles—melting point 134°–134.5° C.).

Analysis: Calculated for $C_{26}H_{28}O_{17}$: C, 50.99; H, 4.61; O, 44.41. Found: C, 50.67; H, 4.52; O, 44.58.

Figure 1:
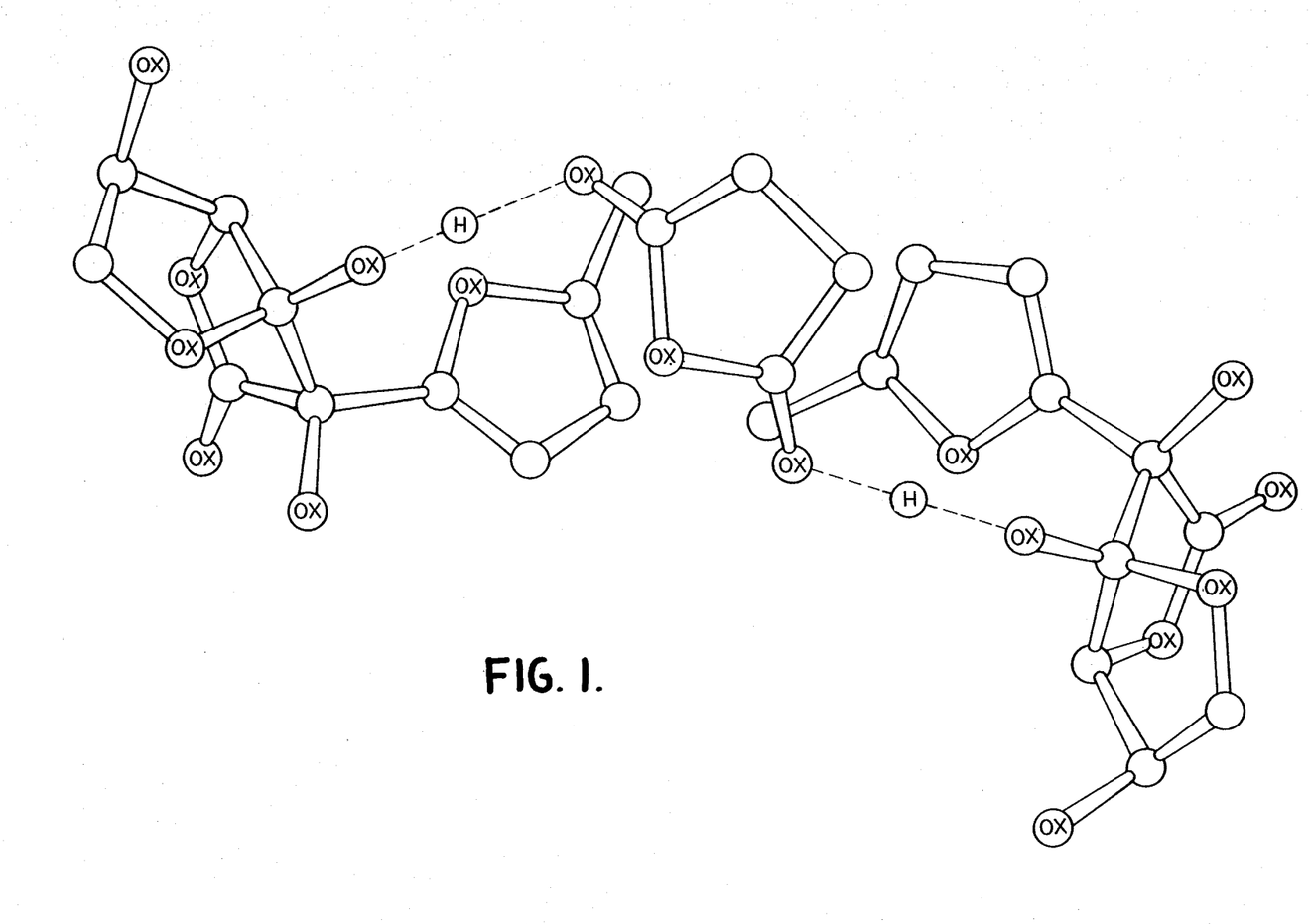
FIG. 1 presents the X-ray crystal structure of the product of Example 1.

X-ray crystallography, FIG. 1, confirmed the structure of the compound and showed the presence of a 2:1, 2-furylbutyrolactone:succinic anhydride, molecular complex in a unit cell.

EXAMPLE 2

186 g 2-methyl-2,5-dimethoxy-dihydrofuran (N. Clauson-Kaas and F. Lindborg (1947) *Acta Chem. Scand.* 1: 619. was added under vigorous mechanical stirring to a solution of 150 g L-ascorbic acid in 1.5 L water at room temperature. The furan was used in 50% excess. The solution became homogenous within 15–20 minutes. The reaction was monitored by a high pressure liquid chromograph equipped with a UV detector. The original peak of Rf 1.6 of L-ascorbic acid at 254 nm in 20% aqueous methanol disappeared while a new peak appeared at Rf 5.9 to 6.0, under 64 atmospheres. It was simultaneously observed that the solution did not consume any more iodine which is indicative of the total disappearance of L-ascorbic acid.

After standing overnight at 20° C. the aqueous solution was freeze-dried to give a pale yellow foam. The latter showed well defined IR, $^{13}C$ NMR and $^{1}H$ NMR spectra.

Next, 119.65 g (0.467 mole—assuming 100% purity) of the crude product (melting point 55° C.) were dissolved in 216 ml of HPLC grade ethylacetate. 23.3 g succinimide (0.235 mole) were added and the mixture was stirred under positive nitrogen pressure. After a few minutes of stirring, a white solid precipitated. The reaction mixture was then heated for 30 min. in an oil bath until the solid redissolved. Heating was stopped and the solution was allowed to cool to room temperature while stirring and then in an ice water bath for 2 hours. A precipitate formed which was filtered by suction, washed with 150 ml of cold chloroform and dried under vacuum to give 67.4 g of crude product (56.3% yield).

The product was recrystallized from a solvent mixture (ethyl acetate/chloroform: 60/40) to give a total yield of 52.2 g (yield 43.6%) of pure product (long white needles—melting point 132°–133° C.).

Analysis: Calculated for $C_{26}H_{29}NO_{16}$: C, 51.07; H, 4.78; O, 41.86; N, 2.29. Found: C, 51.17; H, 4.93; O, 41.81; N, 2.21.

X-ray crystallography, confirmed the structure of the compound and showed the presence of a 2:1, 2-furyl-butyrolactone:succinimide molecular complex in a unit cell.

latter showed well defined IR, $^{13}C$ NMR and $^1H$ NMR spectra.

Next, 10.24 g (0.04M) of the crude product (melting point 55° C.) and 2.5 g (0.022M) of N-methylsuccinimide were placed into a 1 liter round-bottomed flask equipped with a reflux condenser and a nitrogen inlet tube. After adding 20 ml of HPLC-grade ethyl acetate, the reaction mixture was refluxed for 4 hours. The homogeneous solution was cooled to room temperature and then placed in an ice-water bath. A white precipitate formed which was filtered by suction and washed with a few ml of cold ethyl acetate to give 5.20 g of the crude product (yield 50.8%). The filtrate was concentrated to half volume and cooled in an ice-water bath.

The product was recrystallized from a solvent mixture (ethyl acetate/chloroform: 1/1) to give a total yield of 3.21 g (yield 31.3%) of pure product (long white needles—melting point 105°–106.5° C.).

Analysis: Calculated for $C_{27}H_{31}NO_{16}$: C, 51.84; H, 5.00; N, 2.24; O, 40.92. Found: C, 51.98; H, 5.12; N, 2.08; O 40.63.

X-ray crystallography, FIG. 1, confirmed the structure of the compound and showed the presence of a 2:1, 2-furylbutyrolactone:N-methylsuccinimide molecular complex in a unit cell.

EXAMPLE 3

93 g 2-methyl-2,5-dimethoxy-dihydrofuran (N. Clauson-Kaas and F. Lindborg (1947) *Acta Chem. Scand.* 1: 619. was added under vigorous mechanical stirring to a solution of 75 g L-ascorbic acid in 750 ml water at room temperature. The furan was used in 50% excess. The solution became homogenous within 15–20 minutes. The reaction was monitored by a high pressure liquid chromograph equipped with a UV detector. The original peak of Rf 1.6 of L-ascorbic acid at 254 nm in 20% aqueous methanol disappeared while a new peak appeared at Rf 5.9 to 6.0, under 64 atmospheres. It was simultaneously observed that the solution did not consume any more iodine which is indicative of the total disappearance of L-ascorbic acid.

After standing overnight at 20° C. the aqueous solution was freeze-dried to give a pale yellow foam. The

EXAMPLE 4

The compound of Example 1 dissolves completely in 2.38 mM bicarbonate buffered saline (0.85%) to form and succinic anhydride.

EXAMPLE 5

The compound of Example 2 dissolves completely in 2.38 mM bicarbonate buffered saline (0.89%) to form and succinimide.

EXAMPLE 6

The compound of Example 3 dissolves completely in 2.38 mM bicarbonate buffered saline (0.85%) to form and N-methylsuccinimide.

EXAMPLE 7

Single dose $LD_{50}$ in C57BL/6 mice for Cpd. 1 is determined following the method of Spearman and Karber described in *Basic Exercises in Immunochemistry*, 1979. Briefly, 0.5 ml of each dose is given to each of ten mice. The survivors are counted after 3 days and the $LD_{50}$ is calculated using the following formula:

$$\text{Log } LD_{50} = \log \text{ (highest dose tested)} + (\log D)\left[\tfrac{1}{2} - \frac{\Sigma R}{N}\right]$$

where D=fold diferences between doses, R=total number dead, and N=total number of animals tested.

TABLE 1

| Results of Cpd. 1 Single I.P. Dose $LD_{50}$ Determination Using C57BL/6 Strain of Mice | |
|---|---|
| Dose of Cpd. 1 | Number Dead on Day 3 |
| 272 mg/17 g mouse (16,000 mg/kg) | 10 |

TABLE 1-continued

| Results of Cpd. 1 Single I.P. Dose $LD_{50}$ Determination Using C57BL/6 Strain of Mice | |
|---|---|
| Dose of Cpd. 1 | Number Dead on Day 3 |
| 136 mg/17 g mouse (8,000 mg/kg) | 10 |
| 68 mg/17 g mouse (4,000 mg/kg) | 7 |
| 34 mg/17 g mouse (2,000 mg/kg) | 0 |
| 17 mg/17 g mouse (1,000 mg/kg) | 0 |
| Cpd. 1 $LD_{50}$ = 59.2 mg/17 g mouse = 3,480 mg/kg. | |

Purified Cpd. 1 is tested in C57BL/6 mice by single i.p. injection and gives an $LD_{50}$ in excess of 3 g/kg.

EXAMPLE 8

Single oral dose $LD_{50}$ in CD-1 mice and CD rats, obtained from Charles River U.K. Ltd., for Cpd. 1 is determined. Briefly, the compound, 5 g/kg, is dissolved in 0.0238M bicarbonate buffer containing 0.85% sodium chloride, pH 6.8, and administered orally using a constant dose volume of 10 ml/kg. Cpd. 1, dissolved in buffer, or just buffer is administered orally and the mice and rats are observed for 14 days after dosing. After 14 days, the animals are sacrificed and necropsy is performed to check for gross evidence of toxicity.

No deaths or signs of toxicity are observed during this study, indicating a single oral dose $LD_{50}$ for Cpd. 1 in excess of 5 g/kg.

EXAMPLE 9

Two strains of mice, C57BL/6 and $BDF_1$ are treated for seven days with i.p. administration of either 25, 50, 100, 200, or 400 mg/kg of Cpd. 1 or just buffer. This is followed on the eighth day by a lymphocyte stimulation assay.

TABLE 2-A

| Effect of Cpd.*1 In Vivo, as Measured by the Lymphocyte Stimulation Assay, on C57BL/6 Strain of Mice | | | |
|---|---|---|---|
| | Lymphocyte Stimulation Index | | |
| Cpd. 1 Conc. | PHA | Con-A | Control |
| 400 mg/kg | 3.2 | 20.7 | 1.0 |
| 200 mg/kg | 21.3 | 34.0 | 1.0 |
| 100 mg/kg | 17.7 | 40.0 | 1.3 |
| 50 mg/kg | * | 26.0 | 1.0 |
| 0 mg/kg | 17.3 | 16.7 | — |

*No results reported

TABLE 2-B

| Effect of Cpd. 1 In Vivo, as Measured by the Lymphocyte Stimulation Assay, on $BDF_1$ Strain of Mice | | | |
|---|---|---|---|
| | Lymphocyte Stimulation Index | | |
| Cpd. 1 Con. | PHA | Con-A | Control* |
| 400 mg/kg | 1.1 | 0.9 | 0.9 |
| 200 mg/kg | 7.8 | 2.9 | 0.8 |
| 100 mg/kg | 48.7 | 17.9 | 0.7 |
| 50 mg/kg | 52.1 | 21.6 | 0.9 |
| 25 mg/kg | 13.8 | 4.3 | 0.8 |
| 0 mg/kg | 5.5 | 1.6 | — |

*Buffer, pH 8.05

The high dose of 400 mg/kg shows strong suppression of the PHA response in the C57BL/6 mice as well as $BDF_1$ mice, a slight suppression of the Con-A response in the $BDF_1$ mice, and a suppression of the Con-A response in C57BL/6 mice when compared to the 200 mg/kg dose. However, the stimulation of T-lymphocyte proliferation is evident for PHA at doses of 50 and 100 mg/kg in $BDF_1$ mice and at a dose of 200 mg/kg in C57BL/6 mice. The Con-A response in the BDF₁ strain is significantly increased at doses between 50 and 100 mg/kg of Cpd. 1 and in the C57BL/6 strain, it is increased at doses of 50, 100 and 200 mg/kg.

EXAMPLE 10

A comparison is made of the lymphocyte response of C57BL/6 mice treated 4 days with i.p. administration of either 50, 100, 200, 400 or 800 mg/kg of Cpd. 1, 50, 100, 200, 400 or 800 mg/kg of ascorbic acid (AA), or just buffer. This is followed on the fifth day by a lymphocyte stimulation assay.

TABLE 3-A

Effect of AA In Vivo, as measured by the Lymphocyte Stimulation Assay, in C57BL/6 Strain of Mice

| AA Conc. | Lymphocyte Stimulation Index | | |
|---|---|---|---|
| | PHA | Con-A | Control |
| 800 mg/kg | 12.1 | 23.9 | .50 |
| 400 mg/kg | 14.3 | 17.8 | 1.3 |
| 200 mg/kg | 10.0 | 21.1 | 1.3 |
| 100 mg/kg | 17.1 | 19.8 | 1.8 |
| 50 mg/kg | 17.1 | 25.5 | .56 |
| 0 mg/kg | 14.2 | 17.1 | — |

TABLE 3-B

Effect of Cpd. 1 In Vivo, as Measured by the Lymphocyte Stimulation Assay, in C57BL/6 Strain of Mice

| Cpd. 1 Conc. | Lymphocyte Stimulation Index | | |
|---|---|---|---|
| | PHA | Con-A | Control |
| 800 mg/kg | .408 | .612 | .31 |
| 400 mg/kg | 4.8 | 40.0 | 1.0 |
| 200 mg/kg | 42.8 | 67.4 | 1.6 |
| 100 mg/kg | 34.8 | 80.0 | 1.6 |
| 50 mg/kg | * | 52.8 | 1.2 |
| 0 mg/kg | 33.0 | 32.6 | — |

*No results reported.

No statistically significant measurable effect of AA was demonstrable with PHA but a single stimulation of proliferation did occur at 50 mg/kg in the Con-A stimulated group.

In spleen cells treated with PHA, doses of 100 and 200 mg/kg of Cpd. 1 tend to stimulate lymphocyte DNA synthesis. Doses ranging from 400 to 800 suppress DNA synthesis of spleen lymphocytes. In spleen cells treated with Con-A, doses ranging from 50 to 200 mg/kg have a significant stimulatory effect and doses ranging from 400 to 800 mg/kg have a significant antiproliferative effect, particularly the 800 mg/kg dose. These data suggest an immunostimulatory effect of Cpd. 1 at low to median concentrations and an immunosuppressive effect of Cpd. 1 at higher concentrations. Also, the likelihood that ascorbic acid by itself can exert a similar effect to Cpd. 1 is unsupported by these experiments.

EXAMPLE 11

Two strains of mice, C57BL/6 and BALB/c, are treated 4 days with i.p. administration of either 50, 100, 200, or 400 mg/kg of Cpd. 1, or just buffer. This is followed on the fifth day by a lymphocyte stimulation assay.

TABLE 4-A

Effect of Cpd. 1 In Vivo, as Measured by the Lymphocyte Stimulation Assay, in C57BL/6 Strain of Mice

| Cpd. 1 Conc. | Lymphocyte Stimulation Index | | |
|---|---|---|---|
| | PHA | Con-A | Control |
| 400 mg/kg | 14.8 | 30.9 | .61 |
| 200 mg/kg | 25.2 | 41.1 | .93 |
| 100 mg/kg | 17.0 | 22.3 | 1.3 |
| 50 mg/kg | 13.6 | 20.6 | .87 |
| 0 mg/kg | 7.85 | 11.4 | — |

TABLE 4-B

Effect of Cpd. 1 In Vivo, as Measured by the Lymphocyte Stimulation Assay, in BALB/C Strain of Mice

| Cpd. 1 Conc. | Lymphocyte Stimulation Index | | |
|---|---|---|---|
| | PHA | Con-A | Control |
| 400 mg/kg | 6.71 | 18.7 | .90 |
| 200 mg/kg | 7.65 | 20.5 | .76 |
| 100 mg/kg | 5.24 | 21.8 | 1.0 |
| 50 mg/kg | 6.44 | 20.5 | 1.4 |
| 0 mg/kg | 1.76 | 9.87 | — |

In spleens treated with PHA and Con-A, doses of 50, 100 and 200 mg/kg tend to stimulate lymphocyte DNA synthesis in both strains of mice. Doses of 400 mg/kg suppress DNA synthesis of spleen cell lymphocytes when compared to the activity at a dose of 200 mg/kg.

EXAMPLE 12

An in vitro lymphocyte stimulation assay is performed directly on normal spleen lymphocytes removed from five normal C57BL/6 mice, using concentrations of Cpd. 1 of 0.001, 0.01, 0.1, 1.0, or 10 μg test well (5×10⁵ cells/well) or just buffer. Following three days of incubation the assay is completed.

TABLE 5-A

Effect of Cpd. 1 In Vitro, as Measured by the Lymphocyte Stimulation Assay, in C57BL/6 Strain of Mice

| Cpd. 1 Conc. | Lymphocyte Stimulation Index | | |
|---|---|---|---|
| | PHA | Con-A | Control |
| 10 μg/well | .920 | 2.15 | 1.9 |
| 1 μg/well | 53.8 | 178 | 2.6 |
| .1 μg/well | 83.1 | 198 | 3.2 |
| .01 μg/well | 87.5 | 198 | 3.2 |
| .001 μg/well | 80.4 | 198 | 3.8 |
| 0 μg/well | 21.9 | 126 | — |

The results indicate significant stimulation of mitogenesis across a range of doses from 0.001–1.0 μg/well and significant suppression at a dose of 10 μg/well for both PHA and Con-A mitogens. The range of concentration effectiveness in vitro may be the result of exclusion of the influence of the host's metabolic system on drug metabolism.

EXAMPLE 13

Lymphocytes isolated from 5 human volunteers are treated in vitro with PHA and Con-A and either 0.1, 1, 10, 50, or 100 μg/well of Cpd. 1, 0.1, 1, 10, 50, or 100 μg/well of AA, or buffer.

TABLE 6-A

Effect of AA on the In Vitro Lymphocyte Stimulation Assay in Humans

| AA Concentration | Lymphocyte Stimulation Index | |
|---|---|---|
| | PHA | Con-A |
| 100 μg/well | 34.23 | 25.18 |
| 50 μg/well | 35.93 | 23.31 |
| 10 μg/well | 35.10 | 27.35 |

TABLE 6-A-continued

Effect of AA on the In Vitro Lymphocyte Stimulation Assay in Humans

| AA Concentration | Lymphocyte Stimulation Index | |
|---|---|---|
| | PHA | Con-A |
| 1.0 μg/well | 34.69 | 24.76 |
| 0.1 μg/well | 38.29 | 24.37 |
| 0 μg/well | 31.25 | 25.86 |

TABLE 6-B

Effect of Cpd. 1 on the In Vitro Lymphocyte Stimulation Assay in Humans

| Cpd. 1 Concentration | Lymphocyte Stimulation Index | |
|---|---|---|
| | PHA | Con-A |
| 100 μg/well | 0.544 | 0.44 |
| 50 μg/well | 0.40 | 1.33 |
| 10 μg/well | 34.37 | 23.82 |
| 1.0 μg/well | 48.60 | 32.63 |
| 0.1 μg/well | 56.67 | 38.06 |
| 0 μg/well | 39.82 | 26.62 |

There is no significant proliferative or anti-proliferative effect demonstrated for AA alone. Whereas for Cpd. 1, a high dose anti-proliferative effect, at doses of 100 and 50 μg/ml, is followed by a markedly increased lymphocyte response at very low doses of 1 and 0.1 μg/ml. The same profile of results are exhibited for both PHA and Con-A mitogens.

EXAMPLE 14

C57BL/6 mice were treated with four daily i.p. doses of either 50, 100, 200, or 400 mg/kg of Cpd. 1 or just buffer. On the fifth day a lymphocyte stimulation assay was performed.

TABLE 7

Effect of Cpd. 1 In Vivo, as Measured by the Lymphocyte Stimulation Assay, in C57BL/6 Strain of Mice

| Cpd. 1 Conc. | Lymphocyte Stimulation Index | | |
|---|---|---|---|
| | PHA | Con-A | Control |
| 400 mg/kg | 18.7 | 26.4 | .31 |
| 200 mg/kg | 23.2 | 26.3 | .22 |
| 100 mg/kg | 23.8 | 25.4 | .40 |
| 50 mg/kg | 17.0 | 23.0 | 1.1 |
| 0 mg/kg | 14.9 | 19.9 | — |

Stimulation of the response to polyclonal mitogens at doses of Cpd. 1 from 50–400 mg/kg with a maximum response achieved between doses of 100–200 mg/kg for both PHA and Con-A test mitogens was observed. It can also be seen that there was a decrease in the response to PHA at the 400 mg/kg dose when compared to the response at the 200 mg/kg dose. This appears to follow the trend of immunosuppression at high doses.

EXAMPLE 15

The in vivo immunomodulatory effect of Cpd. 1 on C57BL/6 mice was studied.

Mice of the C57BL/6 strain were tested with i.p. administration of either 100, 200, 400 or 600 mg/kg of Cpd. 1 or just buffer. This was followed by removal of spleens and treatment of lymphocytes therein with mitogens PHA and Con-A.

TABLE 8

Effect of Cpd. 1 In Vivo, as Measured by the Lymphocyte Stimulation Assay, on C57BL/6 Strain of Mice

| Cpd. 1 Conc. | Lymphocyte Stimulation Index | | |
|---|---|---|---|
| | PHA | Con-A | Control |
| 600 mg/kg | 17.6 | 26.5 | 1.7 |
| 400 mg/kg | 44.9 | 42.4 | .49 |
| 200 mg/kg | 48.2 | 36.6 | .62 |
| 100 mg/kg | 51.1 | 43.9 | .80 |
| 0 mg/kg | 13.1 | 26.7 | — |

Doses ranging from 100 to 400 mg/kg of Cpd. 1 caused significant stimulation of both the Con-A and PHA treated lymphocytes. The high dose, 600 mg/kg, caused less stimulation than the 100 to 400 mg/kg doses and gave levels comparable to controls. There was no evidence of toxicity in the 600 mg/kg treated animals given the five day administration of Cpd. 1.

EXAMPLE 16

An in vitro lymphocyte stimulation assay was performed using spleen lymphocytes from normal C57BL/6 mice. The lymphocytes were treated with either 1, 5, 10, 50 or 100 μg/well of Cpd. 1 or buffer.

TABLE 9

Effect of Cpd. 1 In Vitro, as Measured by the Lymphocyte Stimulation Assay, in C57BL/6 Strain of Mice

| Cpd. 1 Conc. | Lymphocyte Stimulation Index | | |
|---|---|---|---|
| | PHA | Con-A | Control |
| 100 μg/well | .292 | .308 | .20 |
| 50 μg/well | .261 | 3.78 | .20 |
| 10 μg/well | 126 | 194 | .66 |
| 5 μg/well | 157 | 162 | 1.8 |
| 1 μg/well | 80.4 | 123 | 1.2 |
| 0 μg/well | 59.5 | 122 | — |

Doses of 5 and 10 μg/well caused significant increases in the response to PHA and Con-A while doses of 50 and 100 μg/well caused significant decreases in the lymphocyte response to the mitogens.

EXAMPLE 17

The compound of Example 2, Cpd. 2, was tested in vivo by using C57BL/6 mice and treating them with Cpd. 3 or just buffer for four consecutive days by the i.p. route. On the fifth day a lymphocyte stimulation assay was performed.

TABLE 3-B

Effect of Cpd. 2 In Vivo, as Measured by the Lymphocyte Stimulation Assay, in C57BL/6 Strain of Mice

| Cpd. 2 Conc. | Lymphocyte Stimulation Index | | |
|---|---|---|---|
| | PHA | Con-A | Control |
| 600 mg/kg | 15.8 | 94.0 | 1.5 |
| 400 mg/kg | 12.9 | 109 | 1.3 |
| 200 mg/kg | 11.3 | 99.3 | .69 |
| 100 mg/kg | 15.4 | 105 | 1.5 |
| 50 mg/kg | 15.5 | 96.1 | .88 |
| 0 mg/kg | 11.0 | 75.1 | — |

Cpd. 2 produced only marginal stimulation of Con-A mitogenesis and had no effect on PHA mitogenesis.

EXAMPLE 18

Cpd. 2 was tested using normal spleen lymphocytes from C57BL/6 mice. A lymphocyte stimulation assay was conducted using either 1, 5, 10, 50, or 100 μg/well Cpd. 3 or just buffer.

TABLE 11

Effect of Cpd. 2 In Vitro, as Measured by the Lymphocyte Stimulation Assay, in C57BL/6 Strain of Mice

| Cpd. 2 Conc. | Lymphocyte Stimulation Index | | |
|---|---|---|---|
| | PHA | Con-A | Control |
| 100 μg/well | 3.83 | 144 | .49 |
| 50 μg/well | 45.8 | 218 | .80 |
| 10 μg/well | 38.8 | 164 | 1.1 |
| 5 μg/well | 29.8 | 148 | 1.2 |
| 1 μg/well | 25.4 | 147 | .92 |
| 0 μg/well | 23.5 | 175 | — |

In spleen cells treated with PHA, doses of 50 and 100 μg/well of Cpd. 2 tended to stimulate lymphocyte DNA synthesis. The 100 μg/well dose suppressed DNA synthesis of spleen lymphocytes. In spleen cells treated with Con-A, the 200 μg/well dose had a stimulatory effect and the 400 μg/well doses had an antiproliferative effect.

EXAMPLE 19

Spleen cells from C57BL/6 mice were treated, in vitro, with the crystallizing reagents, succinic acid and succinimide. Since these compounds are spontaneously released from the molecular complex in solution at a molar ratio of 2 moles of Cpds. 1, 2, or 3 per mole of the crystalline reagent, these reagents were treated in the lymphocyte stimulation assay at proper molar concentrations.

TABLE 12-A

Effect of Succinic Acid In Vitro, as Measured by the Lymphocyte Stimulation Assay, in C57BL/6 Strain of Mice

| Succinic Acid Conc. | Lymphocyte Stimulation Index | | |
|---|---|---|---|
| | PHA | Con-A | Control |
| 16.6 μg/well | 11.5 | 38.5 | 1.1 |
| 8.3 μg/well | 12.4 | 35.6 | .91 |
| 4.15 μg/well | 14.0 | 42.3 | .91 |
| 2.08 μg/well | 15.3 | 51.1 | 1.0 |
| 1.04 μg/well | 15.7 | 64.6 | .94 |
| 0 μg/well | 15.9 | 83.5 | — |

TABLE 12-B

Effect of Succinimide In Vivo, as Measured by the Lymphocyte Stimulation Assay, in C57BL/6 Strain of Mice

| Succinimide Acid Conc. | Lymphocyte Stimulation Index | | |
|---|---|---|---|
| | PHA | Con-A | Control |
| 13.92 μg/well | 17.1 | 92.9 | 1.4 |
| 6.96 μg/well | 17.2 | 71.9 | 1.1 |
| 3.48 μg/well | 18.1 | 85.1 | .98 |
| 1.74 μg/well | 17.5 | 83.4 | 1.1 |
| 0.87 μg/well | 19.5 | 76.0 | .91 |
| 0 μg/well | 19.1 | 100 | — |

The lymphocytes treated with succinic acid showed a decrease in PHA and Con-A mitogenesis with increased succinic acid dosage. The succinimide demonstrated no significant suppressive or enhancing effect on the response of the lymphocytes to either mitogen.

EXAMPLE 20

The compound of example 3, Cpd. 3, was used to treat C57BL/6 spleen lymphocytes in vitro. The lymphocytes were treated with either 1, 5, 10, 50, or 100 μg/well of Cpd. 3 or just buffer and then a lymphocyte stimulation assay was performed.

TABLE 13

Effect of Cpd. 3 In Vitro, as Measured by the Lymphocyte Stimulation Assay, in C57BL/6 Strain of Mice

| Cpd. 3 Conc. | Lymphocyte Stimulation Index | | |
|---|---|---|---|
| | PHA | Con-A | Control |
| 100 μg/well | 0.263 | 2.88 | .25 |
| 50 μg/well | 4.08 | 97.2 | .27 |
| 10 μg/well | 24.0 | 89.6 | .47 |
| 5 μg/well | 18.5 | 80.9 | .64 |
| 1 μg/well | 12.5 | 73.2 | .60 |
| 0 μg/well | 12.2 | 94.6 | — |

The 10 μg/well dose of Cpd. 3 significantly stimulated the response to PHA while the 50 and 100 μg/well doses suppressed the response. The 50 μg/well dose slightly stimulated the response to Con-A and the 100 μg/well dose suppressed the response.

EXAMPLE 21

Three month old mice of the SJL/J strain, which are T-cell deficient, are treated with i.p. administration of 100, 200, or 400 mg/kg of Cpd. 1 or just buffer for four days. This is followed by a lymphocyte stimulation assay.

TABLE 14

Effect of Cpd. 1 In Vivo, as Measured by the Lymphocyte Stimulation Assay, in SJL/J Strain of Mice

| Cpd. 1 Conc. | Lymphocyte Stimulation Index | | |
|---|---|---|---|
| | PHA | Con-A | Control |
| 400 mg/kg | 2.31 | 3.30 | 0.693 |
| 200 mg/kg | 1.79 | 4.57 | 0.732 |
| 100 mg/kg | 1.85 | 5.01 | 0.573 |
| 0 mg/kg | 1.11 | 2.4 | — |

EXAMPLE 22

The SJL/J mice apparently shift to a loss of immune regulation function as they age and the latter is evidenced by a hyperresponsiveness to alloantigens and production of circulating antibodies to nuclear material as well as synthetic double stranded RNA and poly I/C. The continuous erosion of immune competence in the SJL/J mice has been observed to extend from birth to death indicating defects in regulatory T-cell subpopulations (possibly suppressor and/or amplifier cells). Because the dynamics of the T-lymphocyte population changes with age, it must be assumed that age plays a role in affecting the results obtained when treating SJL/J mice with Cpd. 1.

An in vivo lymphocyte stimulation assay was performed on SJL/J mice of different ages, either 2, 5, or 10 months. The mice received i.p. injections of either 100 mg/kg of Cpd. 1 or just buffer.

TABLE 15

Effect of Cpd. 1 In Vivo, as Measured by the Lymphocyte Stimulation Assay, in SJL/J Strain of Mice

| Age of Mice (Months) | | Lymphocyte Stimulation Index | | |
|---|---|---|---|---|
| | | PHA | Con-A | Control |
| 2 | 0 mg/kg | 40.8 | 103 | — |
| | 100 mg/kg | 32.6 | 167 | 2.3 |
| 5 | 0 mg/kg | 2.09 | 19.5 | — |
| | 100 mg/kg | 1.16 | 12.9 | 1.9 |
| 10 | 0 mg/kg | 3.97 | 21.9 | — |
| | 100 mg/kg | 9.18 | 14.5 | 2.1 |

The results obtained from the untreated controls demonstrated the age dependent variation of the PHA and Con-A lymphocyte proliferation responses.

Also, at 2 months of age Cpd. 1 administered at a dose of 100 mg/kg caused a decreased PHA versus increased Con-A response. In contrast, at 5 months of age the SJL/J mice given the dose of Cpd. 1 showed a depressed mitogenesis response to both PHA and Con-A. The ten month old SJL/J mice showed a complete reversal and demonstrated significant stimulation of both the PHA and Con-A mitogenic response upon treatment of mice at the same dose.

EXAMPLE 23

Mice of the C57BL/6 strain are given i.p. injections of either 50, 100, 200 or 400 mg/kg of Cpd. 1 or buffer for twelve days (days 1–12). An antigen, bovine serum albumin (BSA), is administered intraperitoneally with Freund's Complete Adjuvant (FCA) on days 1, 7 and 14. Blood samples are taken for assay of the antibody response on days 0, 5, 13, and 19. Also, on days 13 and 10 a lymphocyte proliferation assay is performed on spleen lymphocytes from these same mice using either the BSA antigen as the specific recall antigen (mitogen) at concentrations of 0.01, 0.1, 0.5 or 1.0 µg/well or just buffer.

TABLE 16-A

Enhancement of the Secondary Immune Response to BSA by Cpd. 1, as Measured by Micro-ELISA titer

| Cpd. 1 Conc. | Micro-ELISA Titer | | | |
| --- | --- | --- | --- | --- |
| | Prebleed | Day 5 | Day 13 | Day 19 |
| 400 mg/kg | N/R* | N/R | 1:80 | 1:320 |
| 200 mg/kg | N/R | N/R | 1:80 | 1:1280 |
| 100 mg/kg | N/R | N/R | 1:40 | 1:1280 |
| 50 mg/kg | N/R | N/R | 1:40 | 1:640 |
| 0 mg/kg | N/R | N/R | 1:20 | 1:320 |

*N/R = no response.

TABLE 16-B

Effect of Cpd. 1 In Vivo on the Secondary Immune Response to BSA, as Measured by Lymphocyte Stimulation Assay, in C57BL/6 Strain of Mice, Day 13

| Cpd. 1 Conc. | Lymphocyte Stimulation Index BSA (µg/well) | | | | |
| --- | --- | --- | --- | --- | --- |
| | 0 | 0.01 | 0.1 | 0.5 | 1 |
| 400 mg/kg | 10.9 | 13.7 | 12.8 | 12.3 | 13.8 |
| 200 mg/kg | 10.6 | 14.1 | 15.8 | 13.8 | 14.0 |
| 100 mg/kg | 3.22 | 9.8 | 11.9 | 12.3 | 10.2 |
| 50 mg/kg | 16.5 | 19.9 | 23.1 | 22.9 | 18.2 |
| 0 mg/kg | — | 14.0 | 14.6 | 12.8 | 13.0 |

TABLE 16-C

Effect of Cpd. 1 In Vivo on the Secondary Immune Response to BSA, as Measured by Lymphocyte Stimulation Assay, in C57BL/6 Strain of Mice, Day 19

| Cpd. 1 Conc. | Lymphocyte Stimulation Index BSA (µg/well) | | | | |
| --- | --- | --- | --- | --- | --- |
| | 0 | 0.01 | 0.1 | 0.5 | 1.0 |
| 400 mg/kg | 5.0 | 3.26 | 2.89 | 1.94 | 1.04 |
| 200 mg/kg | 0.42 | 2.94 | 2.82 | 2.56 | 2.12 |
| 100 mg/kg | 4.1 | 3.79 | 2.68 | 2.03 | .26 |
| 50 mg/kg | .26 | 2.33 | 2.27 | 2.37 | 2.63 |
| 0 mg/kg | — | 1.58 | 1.56 | 2.07 | 1.02 |

No antibody response is observed until day 13. On that day, a significant (four-fold) stimulation is observed at Cpd. 1 doses of 200 and 400 mg/kg and only a slight amount of stimulation is observed at doses of 50 and 100 mg/kg of Cpd. 1. A much more dramatic response is observed on day 19. At that time, the antibody responses to BSA are equal at the 0 mg/kg and 400 mg/kg dose of Cpd. 1, and higher than observed on day 13. A slight increase of antibody titer over the control is observed at 50 mg/kg of Cpd. 1 while 100 and 200 mg/kg doses of Cpd. 1 are extremely stimulatory, demonstrating a 16-fold increase over controls.

The second component of Example 23 illustrates the effects of Cpd. 1 on the lymphocyte proliferation of spleen cells to the immunizing antigen (BSA). Only the 50 mg/kg dose shows significant stimulation of DNA synthesis on day 13 compared to controls. This effect has waned by day 19, indicating the importance of sustaining treatment to stimulate the cell-mediated (T-cell) component of the immune response. The above mentioned antibody response is likely to be sustained after cessation of therapy since the half life of IgG (the antibody) in vivo is approximately 5–7 days.

EXAMPLE 24

Mice of the C57BL/6 strain are given i.p. injections of either 50, 100, 200 or 400 mg/kg of Cpd. 1 or buffer for ten days (days 1–10). An antigen, keyhole limpet hemocyanin (KLH), is administered intraperitoneally with Freund's Complete Adjuvant (FCA) on days 1, 7, and 13. Blood samples are taken for assay of the antibody response on days 0, 5, 12, and 17. Spleens are removed, lymphocytes isolated and a lymphocyte stimulation assay with PHA, Con-A or KLH antigen as the mitogens is performed on day 17 of the experiment.

TABLE 17-A

Enhancement of the Secondary Immune Response to KLH by Cpd. 1, as Measured by Micro-ELISA Titer

| Cpd. 1 Conc. | Micro-ELISA Titer | | | |
| --- | --- | --- | --- | --- |
| | Prebleed | Day 5 | Day 12 | Day 17 |
| 400 mg/kg | N/R* | N/R | 1:5120 | 1:10,240 |
| 200 mg/kg | N/R | N/R | 1:5120 | 1:10,240 |
| 100 mg/kg | N/R | N/R | 1:2560 | 1:5120 |
| 50 mg/kg | N/R | N/R | 1:2560 | 1:5120 |
| 0 mg/kg | N/R | N/R | 1:2560 | 1:1280 |

*N/R—no response.

TABLE 17-B

Effect of Cpd. 1 In Vivo on the Response to KLH, PHA and Con-A as Measured by Lymphocyte Stimulation Assay, in C57BL/6 Strain of Mice, Day 17

| Cpd. 1 Conc. | Lymphocyte Stimulation Index KLH (µg/well) | | | |
| --- | --- | --- | --- | --- |
| | 1.0 | 0.5 | 0.05 | 0.025 |
| 400 mg/kg | 0.589 | 0.232 | 0.667 | 1.03 |
| 200 mg/kg | 7.45 | 4.26 | 1.02 | 3.91 |
| 100 mg/kg | 0.898 | 0.734 | 0.526 | 0.401 |
| 50 mg/kg | 0.536 | 0.415 | 0.357 | 0.0386 |
| 0 mg/kg | 0.715 | 0.614 | 0.739 | 1.06 |

| Cpd. 1 Conc. | PHA | Con-A | Control |
| --- | --- | --- | --- |
| 400 mg/kg | 2.32 | 35.5 | 0.840 |
| 200 mg/kg | 12.4 | 51.7 | 1.73 |
| 100 mg/kg | 9.12 | 15.6 | 0.961 |
| 50 mg/kg | 7.65 | 19.0 | 0.976 |
| 0 mg/kg | 11.0 | 34.1 | — |

No antibody response is observed until day 12, when the 200 and 400 mg/kg treatment groups show significant stimulation (four-fold increases) over the control treatment groups. A similar pattern of difference between the controls and treated groups holds on day 17, seven days after cessation of Cpd. 1 treatment, with the 200 and 400 mg/kg doses showing an eight-fold increase over the untreated antigen-sensitized controls.

The lymphocyte proliferation assay is only performed on day 17, some five days subsequent to completion of the Cpd. 1 treatment protocol. A statistically significant increase in lymphocyte DNA synthesis is seen in the 200 mg/kg treated mice stimulated by Con-A or KLH mitogens. The lymphocyte mitogen response to Con-A (T-cell mitogen) correlated well with a positive response to KLH of the KLH sensitized spleen lymphocytes.

EXAMPLE 25

The effect of Cpd. 1 on cytotoxic lymphocyte (CTL) activity is measured using five DBA/2 mice in the early stage of the TDS, 10 days after challenge with viable L5178Y tumor cells. Six doses of Cpd. 1, 0.001, 0.01, 0.1, 1.0, 10, or 100 μg/ml or just buffer are added in 100 μl volumes to MLTC microculture wells containing washed spleen lymphocytes from the DBA/2 mice, effector, and L5178Y target cells at varying $E/T$ ratios. The MLTC reaction is performed in the presence or absence of irradiated L5178Y stimulator cells.

TABLE 18-A

Effect of Cpd. 1 on CTL Activity of TDS Spleen Lymphocytes from DBA/2 Mice, as Measured by MLTC Assay Using Effector Cells Co-cultured with Stimulator Cells

| Cpd. 1 Conc. | % Lysis E/T Ratio | | |
|---|---|---|---|
| | 100:1 | 30:1 | 10:1 |
| 100 μg/ml | 87.3 | 54.2 | 21.2 |
| 10 μg/ml | 74.3 | 42.0 | 15.9 |
| 1.0 μg/ml | 71.5 | 46.0 | 15.6 |
| 0.1 μg/ml | 79.0 | 51.0 | 20.2 |
| 0.01 μg/ml | 77.1 | 55.8 | 20.6 |
| 0.001 μg/ml | 71.1 | 40.2 | 16.7 |
| 0 μg/ml | 55.2 | 23.0 | 8.2 |

TABLE 18-B

Effect of Cpd. 1 on CTL Activity of TDS Spleen Lymphocytes from DBA/2 Strain of Mice, as Measured by MLTC Assay Using Effector Cells Without Stimulator Cells

| Cpd. 1 Conc. | % Lysis E/T Ratio | | |
|---|---|---|---|
| | 100:1 | 30:1 | 10:1 |
| 100 μg/ml | 42.0 | 18.7 | 8.6 |
| 10 μg/ml | 36.3 | 16.8 | 4.6 |
| 1.0 μg/ml | 40.1 | 20.0 | 4.6 |
| 0.1 μg/ml | 31.6 | 14.8 | 3.5 |
| 0.01 μg/ml | 26.0 | 15.7 | 3.5 |
| 0.001 μg/ml | 23.4 | 12.2 | 3.9 |
| 0 μg/ml | 22.7 | 11.0 | −2.2 |

Cpd. 1 causes a significant increase in CTL activity expressed as % lysis at several concentrations irrespective of the $E/T$ ratio employed or whether or not stimulator cells are present.

This data therefore supports amplification of the specific CTL response of TDS mouse spleen cells sensitized to L5178Y tumor cells in a drug dose dependent manner.

EXAMPLE 26

Five DBA/2 mice in the early stage of the TDS, 10 days after challenge with viable L5178Y tumor cells were used to measure the effect of Cpd. 1 on CTL activity. Two doses of Cpd. 1, 10, or 100 μg/ml, or just buffer were added in 100 ul volumes to the MLTC microculture wells containing washed spleen lymphocytes from the DBA/2 mice, effector and L5178Y target cells at varying $E/T$ ratios. The MLTC reaction was performed in the presence or absence of irradiated L5178Y stimulator cells.

TABLE 19-A

Effect of Cpd. 1 on CTL Activity of TDS Spleen Lymphocytes from DBA/2 Mice, as Measured by MLTC Assay Using Effector Cells Co-cultured with Stimulator Cells

| Cpd. 1 Conc. | % Lysis E/T Ratio | | | |
|---|---|---|---|---|
| | 50:1 | 25:1 | 12.5:1 | 6.25:1 |
| 100 μg/ml | 71.6 | 79.8 | 75.7 | 56.3 |
| 10 μg/ml | 75.7 | 72.0 | 67.1 | 60.5 |
| 0 μg/ml | 63.9 | 61.9 | 45.0 | 35.5 |

TABLE 19-B

Effect of Cpd. 1 on CTL Activity of TDS Spleen Lymphocytes from DBA/2 Strain of Mice, as Measured by MLTC Assay Using Effector Cells Without Stimulator Cells

| Cpd. 1 Conc. | % Lysis E/T Ratio | | | |
|---|---|---|---|---|
| | 50:1 | 25:1 | 12.5:1 | 6.25:1 |
| 100 μg/ml | 21.8 | 16.6 | 11.1 | 6.1 |
| 10 μg/ml | 12.8 | 8.1 | 6.9 | .7 |
| 0 μg/ml | −7.5 | −3.0 | −3.5 | −1.3 |

Cpd. 1 caused a significant increase in CTL activity expressed as % lysis, at several concentrations irrespective of the $E/T$ ratio employed or whether or not stimulator cells were present.

EXAMPLE 27

DBA/2 mice in the early stage of TDS, prior to challenge with viable L5178Y tumor cells, were used to measure the effect of Cpd. 2 on CTL activity. Cpd. 2, 0.1, 1.0, 10 or 100 μg/ml, or just buffer was added in 100 ul volumes to MLTC microculture wells containing washed spleen lymphocytes from DBA/2 mice, effector, and L5178Y target cells at varying $E/T$ ratios. The MLTC reaction was performed in the presence or absence of irradiated L5178Y stimulator cells.

TABLE 20-A

Effect of Cpd. 2 on CTL Activity of Pre-Challenge TDS Spleen Lymphocytes from DBA/2 Mice, as Measured by MLTC Assay Using Effector Cells Co-cultured with Stimulator Cells

| Cpd. 2 Conc. | % Lysis E/T Ratio | | | |
|---|---|---|---|---|
| | 100:1 | 50:1 | 25:1 | 12.5:1 |
| 100 μg/ml | 78.5 | 73.5 | 65.0 | 47.0 |
| 10 μg/ml | 73.5 | 72.5 | 72.5 | 58.5 |
| 1 μg/ml | 75.5 | 72.5 | 69.5 | 58.0 |
| 0.1 μg/ml | 74.5 | 69.5 | 64.0 | 47.5 |
| 0 μg/ml | 68.5 | 67.0 | 57.0 | 37.5 |

TABLE 20-B

Effect of Cpd. 2 on CTL Activity of Pre-Challenge TDS Spleen Lymphocytes from DBA/2 Mice, as Measured by MLTC Assay Using Effector Cells Without Stimulator Cells

| Cpd. 2 Conc. | % Lysis E/T Ratio | | | |
|---|---|---|---|---|
| | 100:1 | 50:1 | 25:1 | 12.5:1 |
| 10 μg/ml | 61.5 | 56.5 | 40.0 | 26.5 |
| 0.1 μg/ml | 48.0 | 43.5 | 29.5 | 16.5 |
| 0 μg/ml | 58.5 | 49.0 | 32.5 | 19.5 |

Cpd. 2 caused an increase in CTL activity, expressed as % lysis, at several concentrations irrespective of the $E/T$ ratio employed or whether or not stimulator cells were present. The one exception was the 0.1 μg/ml dose when no stimulator cells were present.

EXAMPLE 28

An MLTC assay is performed to assess the CTL activity and tumor target cell specificity of Cpd. 1. Tumor dormant spleen cells and normal spleen cells of DBA/2 mice are used as effector cells. Irradiated L5178Y cells are used as stimulator cells. $^{51}$Cr-labeled L5178Y cells and FLC-745 cells are used as target cells. The effector/target ratios studied are 100:1, 30:1 and 10:1.

TABLE 21

Effect of Cpd. 1 In Vitro, as Measured by MLTC Assay, on TDS and Normal Spleen Cells from the DBA/2 Strain of Mice

|  | % Lysis E/T Ratio | | |
| --- | --- | --- | --- |
|  | 100:1 | 30:1 | 10:1 |
| Target cell - L5178Y | | | |
| E + S + D | 82.3 | 69.2 | 34.9 |
| E + S | 55.5 | 39.3 | 11.4 |
| E + D | 52.8 | 29.8 | 9.0 |
| E | 50.9 | 29.2 | 7.2 |
| N + S + D | −9.5 | −9.7 | −10.9 |
| N + S | −14.2 | −10.5 | −11.2 |
| N + D | −12.4 | −11.4 | −10.3 |
| N | −11.2 | −11.0 | −10.9 |
| Target cell - FLC-745 | | | |
| E + S + D | 13.4 | 3.6 | 0.5 |
| E + S | 6.9 | 1.4 | −4.0 |
| E + D | 6.6 | 4.6 | 0.7 |
| E | 11.8 | 6.6 | −1.3 |
| N + S + D | 5.8 | −0.8 | −1.1 |
| N + S | 5.8 | 1.1 | −2.6 |
| N + D | 13.9 | 0.9 | −3.5 |
| N | 1.7 | −1.8 | −2.9 |

E = Effector, Tumor dormant spleen cells; S = Stimulator, Irradiated L5178Y cells; D = Cpd. 1; N = Normal effector cells, Normal spleen cells.

A significant specific enhancement of CTL activity of effector cells in the presence of stimulator cells was noted in the L5178Y target control system when Cpd. 1 is present. This effect is not observed in the FLC-745 target control system nor did effector cells alone yield an enhancement effect. These results demonstrate the enhancement of the activity of stimulated effector cells by Cpd. 1, the activity of the T-cell memory of the system, and the specificity of the stimulated effector cells.

EXAMPLE 29

The effect of Cpd. 1 on the establishment of the L5178Y tumor dormant state is studied by treating forty DBA/2 mice with Cpd. 1 after the mice have undergone the TDS inducing procedure. Two days after the mice have been challenged with i.p. administration of 50,000 viable L5178Y tumor cells, twenty of these mice receive seven consecutive days of i.p. treatment with Cpd. 1 at 100 mg/kg and the remaining twenty mice receive buffer only. A partial peritoneal lavage is performed twenty-five days after the last dose of Cpd. 1 and the peritoneal exudate fluid is plated out for determination of tumor cell numbers (tumor cell quantitative assay). Survival time is recorded out to 90 days after challenge with the viable L5178Y tumor cells. The percent mortality is calculated for each group.

TABLE 22-A

Range Distribution of Tumor Cells in TDS DBA/2 Mice, as Measured by Tumor Cell Quantitative Assay

|  | Control Group | | Treated Group | |
| --- | --- | --- | --- | --- |
| No. Tumor Cells | Frequency | % of Total | Frequency | % of Total |
| 0 | 1 | 6 | 4 | 22 |
| <1,000 | 6 | 35 | 6 | 33 |
| 1,000 to 100,000 | 8 | 47 | 7 | 39 |
| >100,000 | 2 | 12 | 1 | 6 |

TABLE 22-B

Mortality Statistics for TDS DBA/2 Mice at 90 Days Post-Challenge

| Cpd. 1 Concentration | No. Survivors | % Survival |
| --- | --- | --- |
| 100 mg/kg | 10 | 55.6 |
| 0 mg/kg | 3 | 17.6 |

There is significant reduction in the numbers of tumor cells recovered from Cpd. 1 treated animals versus the controls. The treated group shows more mice demonstrating lower tumor cell numbers in peritoneal washes. There is a significantly greater survival of these mice treated with Cpd. 1 over untreated controls.

EXAMPLE 30

The effect of Cpd. 1 on the establishment of the L5178Y tumor dormant state was studied by treating forty DBA/2 mice with Cpd. 1 after the mice had undergone the TDS inducing procedure. Two days after the mice were challenged with i.p. administration of 50,000 viable L5178Y tumor cells, twenty of these mice received seven consecutive days of i.p. treatment with Cpd. 1 at 100 mg/kg and the remaining twenty mice received buffer only. A partial peritoneal lavage was performed twenty-five days after the last dose of Cpd. 1 and the peritoneal exudate fluid was plated out for determination of tumor cell numbers (tumor cell quantitative assay). Survival time was recorded out to 114 days after challenge with the viable L5178Y tumor cells. The percent mortality was calculated for each group.

TABLE 23-A

Range Distribution of Tumor Cells in TDS DBA/2 Mice, as Measured by Tumor Cell Quantitative Assay

|  | Control Group | | Treated Group | |
| --- | --- | --- | --- | --- |
| No. Tumor Cells | Frequency | % of Total | Frequency | % of Total |
| 0 | 3 | 13.0 | 16 | 69.6 |
| <1,000 | 8 | 34.8 | 2 | 8.7 |
| 1,000 to 100,000 | 10 | 43.5 | 4 | 17.4 |
| >100,000 | 2 | 8.7 | 1 | 4.3 |

TABLE 23-B

Mortality Statistics for TDS DBA/2 Mice at 114 Days Post-Challenge

| Cpd. 1 Concentration | No. Survivors | % Survival |
| --- | --- | --- |
| 100 mg/kg | 19 | 82.6 |
| 0 mg/kg | 11 | 47.8 |

There was significant reduction in the numbers of tumor cells recovered from Cpd. 1 treated animals versus the controls. The treated group showed more mice demonstrating lower tumor cell numbers in peritoneal washes. There was a significantly greater survival of mice treated with Cpd. 1 over untreated controls.

EXAMPLE 31

Mice of the $BDF_1$ strain, inoculated with L-1210 leukemia cells, are treated for seven days with either 25, 50, 100, 200 or 400 mg/kg of Cpd. 1 or just buffer. The National Cancer Institute protocol for screening new anti-cancer agents is followed and T/C ratios are calculated.

TABLE 24

Effect of Cpd. 1 on the Treatment of L-1210 Leukemia, as Measured by T/C Ratios, in $BDF_1$ Strain of Mice

| Cpd. 1 Conc. | Median Survival Time (Days) | T/C |
| --- | --- | --- |
| 400 mg/kg | 25 | 1.25 |
| 200 mg/kg | 30 | 1.50 |
| 100 mg/kg | 30 | 1.50 |
| 50 mg/kg | 21 | 1.05 |
| 25 mg/kg | 20 | 1.00 |
| 0 mg/kg | 20 | — |

The doses of 400, 200 and 100 mg/kg yield T/C values of 1.25, 1.50 and 1.50 respectively, which are considered significant by National Cancer Institute standards of evaluation.

EXAMPLE 32

Mice of the $BDF_1$ strain, inoculated with L-1210 leukemia cells, are treated for seven days with either 100 mg/kg of Cpd. 1, 20 mg/kg of 5-flourouracil (5-FU), a known anti-cancer agent, or just buffer. The National Cancer Institute protocol for screening new anti-cancer agents is followed and T/C ratios are calculated.

TABLE 25

Effect of Cpd. 1 and 5-FU on the Treatment of L-1210 Leukemia, as Measured by T/C Ratios, in $BDF_1$ Strain of Mice

| Drug | Conc. | Median Survival Time | T/C |
| --- | --- | --- | --- |
| Cpd. 1 | 100 mg/kg | 28 | 1.40 |
| 5-FU | 20 mg/kg | 30 | 1.50 |
| Buffer | | 20 | — |

The 100 mg/kg Cpd. 1 treatment dose yields a T/C value of 1.40 compared to 1.50 for the 5-FU positive control. This data substantiated the positive findings of Example 31 and also compares the anti cancer results observed after use of Cpd. 1 to the results observed after use of an accepted positive control drug, 5-FU.

What is claimed is:

1. A method for modulating in stimulation or suppression mode the lymphocyte system of mammals comprising administering a composition comprising a modulatorily effective amount of a compound of the formula:

wherein:
$R_2$ is selected from the group consisting of hydrogen and lower alkyl;
$R_5$ and $R_6$ are selected from the group consisting of hydrogen and lower alkyl and may be the same or different;
$R_8$ is selected from the group consisting of hydrogen and lower alkyl;
$R_7$ is hydrogen, lower alkyl or $R_9$ is $CH_2OH$
$R_{10}$ is hydrogen;
when $R_7$ contains a hydroxyl group in the α or β position, $R_7$ may form the hemiketal ring closure at carbon 3 of the butyrolactone with protonation of the carbonyl group on the same carbon atom and X is selected from the group consisting of O, S and NH the low dosage corresponding to the stimulatory mode of modulation and the high dosages corresponding to the suppression mode of modulation and a pharmaceutically acceptable carrier therefor.

2. The method of claim 1, wherein:
$R_2$ is —$CH_3$;
$R_5$ and $R_6$ are each hydrogen;
X is O;
$R_9$ is —$CH_2OH$; and
$R_7$ forms the hemiketal ring closure at carbon 3 of the butyrolactone with protonation of the carbonyl group at carbon 3.

3. The method of claim 1, wherein said pharmaceutical carrier comprises a buffered, isotonic saline solution.

4. The method of claim 1, wherein the lymphocyte system in mammals is suppressed, comprising administering a composition comprising a suppressively effective amount of a compound of claim 1 and a pharmaceutically acceptable carrier therefor.

5. The method of claim 4, wherein said composition is administered in a therapeutic dosage comprising about 300 to 1,000 mg per kg of body weight.

6. The method of claim 4, wherein said composition is administered in a preferred dosage comprising about 400 to 800 mg per kg of body weight.

7. The method of claim 1, wherein the lymphocyte system in mammals is stimulated, comprising administering a composition comprising a stimulatory effective amount of a compound of claim 1 and a pharmaceutically acceptable carrier therefor.

8. The method of claim 7, wherein said composition is administered in the therapeutic dosage comprising about 10 to 300 mg per kg of body weight.

9. The method of claim 7, wherein said composition is administered in a preferred dosage comprising about 50 to 200 mg per kg of body weight.

10. The method of claim 1, wherein said composition is administered in a therapeutic dosage comprising about 10 to 1,000 mg per kg of body weight.

11. The method of claim 1, wherein said administration of said composition is by intraperitoneal injection.

12. The method of claim 1, wherein said administration of said composition is oral.

13. The method of claim 1, wherein said administration of said composition is subcutaneous.

14. The method of claim 1, wherein said administration of said composition is intravenous.

15. The method of claim 1, wherein said administration of said composition is intramuscular.

16. The method of claim 1 wherein the chemotoxic or phagocytoxic response of components of said lymphocyte ststem is stimulated by administering an effective amount of a compound of claim 1 and a pharmaceutically acceptable carrier therefor.

* * * * *